United States Patent [19]

Markwell et al.

[11] Patent Number: 4,745,115
[45] Date of Patent: * May 17, 1988

[54] ISOQUINOLINES OR BENZISOQUINOLINER HAVING ANTIINFLAMMATORY ACTIVITY

[75] Inventors: Roger E. Markwell, Great Dunmow; Stephen A. Smith; David J. Hunter, both of Bishop's Stortford, all of England

[73] Assignee: Beecham Group p.l.c., Brentford, England

[*] Notice: The portion of the term of this patent subsequent to Mar. 25, 2003 has been disclaimed.

[21] Appl. No.: 789,105

[22] Filed: Oct. 18, 1985

[30] Foreign Application Priority Data

Oct. 19, 1984 [GB] United Kingdom ............. 8426584

[51] Int. Cl.$^4$ .................. A61K 31/47; C07D 217/22; C07D 221/08; C07D 221/10
[52] U.S. Cl. .................. 514/226.8; 514/290; 514/310; 514/228.2; 514/228.8; 514/232.8; 514/235.2; 544/126; 544/128; 546/101; 546/143
[58] Field of Search .......... 546/101, 141, 143, 90, 546/83, 65; 544/128, 126; 514/237, 290, 309, 310, 229, 231, 232, 234, 236

[56] References Cited

U.S. PATENT DOCUMENTS

| | | | |
|---|---|---|---|
| 2,168,929 | 8/1939 | Bockmühl et al. | 546/90 X |
| 2,653,940 | 9/1953 | Johnson | 546/159 X |
| 3,946,018 | 3/1976 | Deák et al. | 546/141 |
| 3,980,655 | 9/1976 | Kunstmann et al. | 546/141 |
| 4,282,222 | 8/1981 | Bartmann et al. | 546/143 X |
| 4,282,223 | 8/1981 | Bartmann et al. | 544/128 X |
| 4,421,920 | 12/1983 | Badouin et al. | 546/163 |
| 4,482,560 | 11/1984 | Banno et al. | 514/312 |
| 4,578,393 | 3/1986 | Markwell et al. | 514/310 |
| 4,604,397 | 8/1986 | Hutchison | 514/291 |

OTHER PUBLICATIONS

Newbould, B. B., *Brit. J. Pharmacol.*, 21, 127–36, (1963).
Vinegar, R. et al., *Federation Proceedings*, 41, 2588–95, (1982); and
Wood, D. D. et al., *Arthritis and Rheumatism*, 26, 975–83, (1983).
Karsten, V. and Wollenberger, A., *Anal. Biochem.*, 77, 464–70, (1977).
Knyazeva, V. F. et al., *Khim–Farm Zh.*, 15(5), 44–49, (1982); and
Moffet, R. B. et al., *J. Het. Chem.*, 16, 1459–67, (1979).
Czuros, Z. et al., *Acta. Chim. Acad. Sci. Hung.*, 60 (1–2), 177–90, (1969).
Gribble, G. W., and Saulnier, M. G., *Tetrahedron Letters*, 21, 4137–40, (1980).
Hazai, L. et al., *Acta. Chim. Acad. Sci. Hung.*, 102(3), 305–15, (1979).
Hazai, L. et al., *Acta. Chim. Acad. Sci. Hung.*, 108(3), 255–63, (1981).
Hazai, et al., Chemical Abstracts, vol. 93, 204420s, (1980).
Tikk, et al. Chemical Abstracts, vol. 95, 80684a, (1981).
Hazai, et al., Chemical Abstracts, vol. 97, 38824n, (1982).
Tikk, et al., Chemical Abstracts, vol. 100, 120854m, (04/09/84).

*Primary Examiner*—Donald G. Daus
*Assistant Examiner*—Diana G. Rivers
*Attorney, Agent, or Firm*—James F. Haley, Jr.; Teresa L. Solomon

[57] ABSTRACT

Compounds of the general formula I

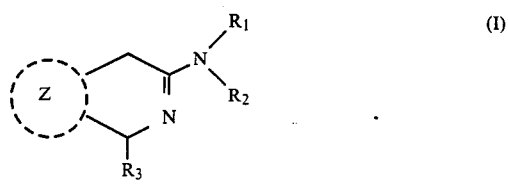

in which:

$R_1$ and $R_2$ are independently hydrogen, $C_{1-6}$ alkyl or together are a group X which is $C_{3-6}$ polymethylene optionally in which one carbon atom is replaced by O, S or $NR_6$ wherein $R_6$ is hydrogen or $C_{1-6}$ alkyl;

$R_3$ is a mono- or fused bi-cyclic heteroaromatic group having up to ten atoms in the aromatic ring(s), not more than four of which are selected from nitrogen, oxygen or sulphur, optionally C-substituted by one or more substituents selected from halogen, $CF_3$, nitro, $C_{1-6}$ alkyl, $C_{1-6}$ alkoxy, $C_{1-6}$ alkylthio, $C_{2-7}$ alkanoyl or cyano; or is phenyl or naphthyl, optionally substituted by one or more substituents selected from halogen, $CF_3$, nitro, $C_{1-6}$ alkyl, $C_{1-6}$ alkoxy, $C_{1-6}$ alkylthio, $C_{2-7}$ alkanoyl, carboxyl, $C_{1-6}$ alkoxycarbonyl, cyano, $CONR_7R_8$ wherein $R_7$ and $R_8$ are selected from hydrogen or $C_{1-6}$ alkyl or together are a group X; $NR_9R_{10}$ wherein $R_9$ and $R_{10}$ are selected from hydrogen, $C_{1-6}$ alkyl, $C_{2-7}$ alkanoyl or $C_{1-6}$ alkylsulphonyl or together are a group X; $SO_2NR_{11}R_{12}$ wherein $R_{11}$ and $R_{12}$ are selected from hydrogen or $C_{1-6}$ alkyl or together are a group X; or $S(O)_mR_{13}$ wherein m is 1 or 2 and $R_{13}$ is $C_{1-6}$ alkyl; Z is naphthyl or a mono- or fused bicyclic heteroaromatic ring having up to ten atoms in the aromatic ring(s), not more than four of which are selected from nitrogen, oxygen or sulphur or (when $R_3$ is an optionally substituted naphthyl or heteroaromatic group as defined) Z is a phenyl ring; and Z is optionally C-substituted by one or two substituents $R_4$ and $R_5$ which are independently selected from $C_{1-6}$ alkyl, cyano, amino, aminocarbonyl or aminocarbamoyl optionally substituted by one or two $C_{1-6}$ alkyl groups or by a group X, halogen, $CF_3$, nitro, $C_{1-6}$ alkoxy, $C_{1-6}$ alkylthio, $C_{2-7}$ alkanoyloxy or hydroxy, or together on adjacent carbon atoms are methylenedioxy or $C_{3-5}$ polymethylene, are disclosed as an active therapeutic substances for the treatment of inflammatory conditions.

10 Claims, No Drawings

ISOQUINOLINES OR BENZISOQUINOLINER HAVING ANTIINFLAMMATORY ACTIVITY

This invention relates to novel compounds having pharmacological activity, to a process for their preparation, to pharmaceutical compositions containing them and to their use in the treatment of mammals.

Khim-Farm Zh. 15(5) 44 (1981) discloses dihydroisoquinoline derivatives of formula (A):

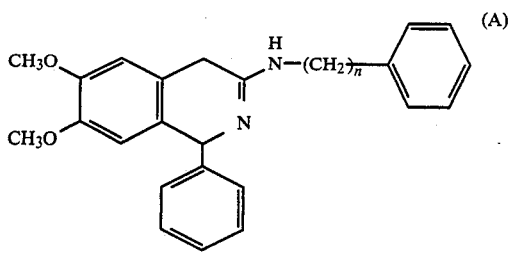

wherein n is 1 or 2. No pharmacological activity has been disclosed for these compounds.

A novel class of compounds which are dihydroisoquinoline derivatives has now been discovered, which compounds have potential utility in the treatment of inflammatory and/or rheumatic and/or allergic conditions.

Accordingly, the present invention provides a compound of formula (I) or a salt or solvate thereof:

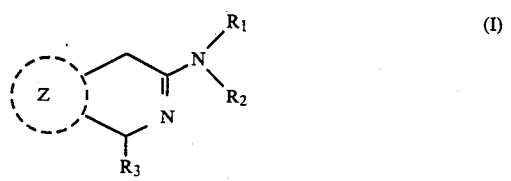

wherein:

$R_1$ and $R_2$ are independently hydrogen, $C_{1-6}$ alkyl or together are a group X which is $C_{3-6}$ polymethylene optionally in which one carbon atom is replaced by O, S or $NR_6$ wherein $R_6$ is hydrogen or $C_{1-6}$ alkyl;

$R_3$ is a mono- or fused bi-cyclic heteroaromatic group having up to ten atoms in the aromatic ring(s), not more than four of which are selected from nitrogen, oxygen or sulphur, optionally C-substituted by one or more substituents selected from halogen, $CF_3$, nitro, $C_{1-6}$ alkyl, $C_{1-6}$ alkoxy, $C_{1-6}$ alkylthio, $C_{2-7}$ alkanoyl or cyano; or is phenyl or naphthyl, optionally substituted by one or more substituents selected from halogen, $CF_3$, nitro, $C_{1-6}$ alkyl, $C_{1-6}$ alkoxy, $C_{1-6}$ alkylthio, $C_{2-7}$ alkanoyl, carboxyl, $C_{1-6}$ alkoxycarbonyl, cyano, $CONR_7R_8$ wherein $R_7$ and $R_8$ are selected from hydrogen or $C_{1-6}$ alkyl or together are a group X; $NR_9R_{10}$ wherein $R_9$ and $R_{10}$ are selected from hydrogen, $C_{1-6}$ alkyl, $C_{2-7}$ alkanoyl or $C_{1-6}$ alkylsulphonyl or together are a group X; $SO_2NR_{11}R_{12}$ wherein $R_{11}$ and $R_{12}$ are selected from hydrogen or $C_{1-6}$ alkyl or together are a group X; or $S(O)_m R_{13}$ wherein m is 1 or 2 and $R_{13}$ is $C_{1-6}$ alkyl;

the ring Z is naphthyl or a mono- or fused bicyclic heteroaromatic ring having up to ten atoms in the aromatic ring(s), not more than four of which are selected from nitrogen, oxygen or sulphur or (when $R_3$ is an optionally substituted naphthyl or heteroaromatic group as defined) Z is a phenyl ring; and Z is optionally C-substituted by one or two substituents $R_4$ and $R_5$ which are independently selected from $C_{1-6}$ alkyl, cyano, amino, aminocarbonyl or aminocarbamoyl optionally substituted by one or two $C_{1-6}$ alkyl groups or by a group X, halogen, $CF_3$, nitro, $C_{1-6}$ alkoxy, $C_{1-6}$ alkylthio, $C_{2-7}$ alkanoyloxy or hydroxy, or together on adjacent carbon atoms are methylenedioxy or $C_{3-5}$ polymethylene.

Suitable values for $R_1$ and $R_2$ include hydrogen, methyl, ethyl, n- and iso-propyl, n-, sec and tert-butyl, or $R_1$ and $R_2$ together are $X^1$ which is $C_4$ or $C_5$ polymethylene or $-(CH_2)_2-O-(CH_2)_2-$. Preferably $R_1$ is hydrogen or methyl and $R_2$ is methyl.

Suitable values for $R_3$ include phenyl, naphthyl, furyl, thienyl, pyrryl, pyridyl, benzofuranyl, benzothienyl and indolyl optionally substituted by one or more of fluoro, chloro, bromo, $CF_3$, nitro, methyl, ethyl, n- and iso-propyl, n-, sec- and tert-butyl, methoxy, ethoxy, n- and iso-propoxy, (when $R_3$ is phenyl or naphthyl) methylthio, ethylthio, n- and iso-propylthio, acetyl, propionyl, carboxyl, methoxycarbonyl, ethoxycarbonyl, cyano, $CONH_2$, $NR_9{}^1R_{10}{}^1$ wherein $R_9{}^1$ and $R_{10}{}^1$ are selected from hydrogen, methyl, methylsulphonyl or together are a group $X^1$ as defined; $SO_2NR_{11}{}^1R_{12}{}^1$ wherein $R_{11}{}^1$ and $R_{12}{}^1$ are selected from hydrogen or methyl, methylsulphonyl, ethylsulphonyl, methylsulphinyl or ethylsulphinyl. Favourably $R_3$ is phenyl or 1- or 2-naphthyl optionally substituted by one or two of fluoro, chloro, bromo, $CF_3$, nitro, methyl, cyano, methoxy, or methylthio. Preferably $R_3$ when optionally substituted phenyl is 2-chlorophenyl, 2-bromophenyl, 2-fluorophenyl or 2-chloro-6-fluorophenyl.

Suitable values for Z include naphthyl, furyl, thienyl, pyrryl, pyridyl, benzofuranyl, benzothienyl and indolyl, or (when $R_3$ is an optionally substituted naphthyl or heteroaromatic group as defined), phenyl; and Z is optionally C-substituted by one or two substituents $R_4{}^1$ and $R_5{}^1$ which are selected from methyl, ethyl, n- and iso-propyl, cyano, amino, aminocarbonyl or aminocarbamoyl optionally substituted by one or two methyl groups, fluoro, chloro, bromo, nitro, methoxy, hydroxy, acetoxy, n-butyryloxy or 2,2-dimethylpropionyloxy, or together on adjacent carbon atoms are methylenedioxy. Favourably $R_4{}^1$ and $R_5{}^1$ are selected from hydrogen, halogen or hydroxy when Z is substituted phenyl, or naphthyl. When Z is naphthyl it may be fused at the 1-2, 2-3, or 3-4 positions.

There is a group of compounds within formula (I) of formula (II):

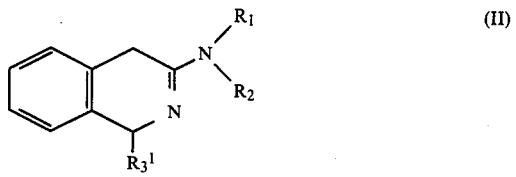

wherein $R_3{}^1$ is naphthyl or pyridyl optionally substituted by one or two of halo, nitro, cyano or methyl; and the remaining variables are as defined in formula (I).

Suitable and preferred values for $R_1$, $R_2$ and $R_3{}^1$ are as described for the corresponding variables in formula (I).

There is a favoured sub-group of compounds within formula (II) of formula (III):

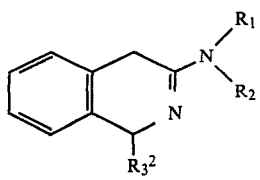

wherein $R_3{}^2$ is naphthyl substituted by one or two of fluoro, chloro or bromo, or pyridyl and $R_1$ and $R_2$ are are as defined in formula (I), being preferably methyl.

There is a further group of compounds within formula (I) of formula (IV):

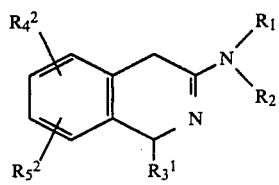

wherein $R_4{}^2$ is hydrogen, halogen, $C_{1-6}$ alkoxy, $C_{2-7}$ alkanoyloxy or hydroxy and $R_5{}^2$ is $C_{1-6}$ alkoxy, $C_{2-7}$ alkanoyloxy or hydroxy; or $R_4{}^2$ and $R_5{}^2$ together are methylenedioxy; and $R_3{}^1$ is as defined in formula (II).

Suitable and preferred values for the variable groups are as described for the corresponding variables under formula (I). $R_3{}^1$ is preferably $R_3{}^2$ as defined in formula (III).

There is a further group of compounds within formula (I) of formula (V):

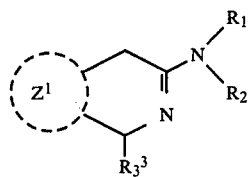

wherein $Z^1$ is naphthyl optionally substituted as defined in formula (I), $R_3{}^3$ is phenyl or pyridyl optionally substituted by one or two of halo, nitro, cyano or methyl and $R_1$ and $R_2$ are as defined in formula (I).

$Z^1$ is favorably naphthyl or naphthyl substituted by one or two chlorine, fluorine or bromine atoms.

Other suitable and preferred values for the $R_1$, $R_2$ and $R_3{}^3$ are as described for the corresponding variables under formula (I).

The compounds of formula (I) or their salts or solvates are preferably in pharmaceutically acceptable form. By pharmaceutically acceptable form is meant, inter alia, of a pharmaceutically acceptable level of purity excluding normal pharmaceutical additives such as diluents and carriers, and including no material considered toxic at normal dosage levels. A pharmaceutically acceptable level of purity will generally be at least 50% excluding normal pharmaceutical additives, preferably 75%, more preferably 90% and still more preferably 95%. One preferred pharmaceutically acceptable form is the crystalline form, including such form in a pharmaceutical composition. In the case of salts and solvates the additional ionic and solvent moieties must also be non-toxic.

Examples of a pharmaceutically acceptable salt of a compound of formula (I) include the acid addition salts for example the hydrochloride and hydrobromide salts.

Examples of a pharmaceutically acceptable solvate of a compound of formula (I) include the hydrate.

The compounds of the formula (I) can form acid addition salts with acids, such as the conventional pharmaceutical acids, for example, maleic, hydrochloric, hydrobromic, phosphoric, acetic, fumaric, salicylic, citric, lactic, mandelic, tartaric, succinic, benzoic, ascorbic and methanesulphonic. Such pharmaceutically acceptable salts form an aspect of this invention.

Where compounds of formula (I) form solvates such as hydrates, these also form an aspect of the invention.

The compounds of formula (I) have at least one asymmetric centre and therefore exist in more than one stereoisomeric form. The invention extends to all such forms and to mixtures thereof, including racemates.

The present invention also provides a process for the preparation of a compound of formula (I), which process comprises the reaction of a compound of formula (VI):

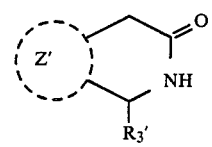

wherein $R_3'$ and $Z'$ are $R_3$ and $Z$ as defined for formula (I) or groups or atoms convertible thereto; with either
(i) $R_1'R_2'NCOQ_1$ wherein $Q_1$ is a leaving group or
(ii) (a) an alkylating agent or (b) a halogenating agent followed by treatment with $R_1'R_2'NH$ wherein $R_1'$ and $R_2'$ are $R_1$ and $R_2$ as defined for formula (I) or groups or atoms convertible thereto;
to form a compound of formula (Ia):

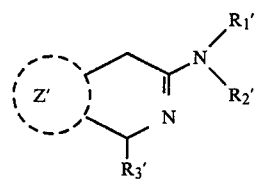

and thereafter where appropriate converting $R_1'$ and/or $R_2'$ to $R_1$ and/or $R_2$ respectively and converting $R_3'$ and/or $Z'$ to $R_3$ and/or $Z$ respectively; and optionally forming a salt or solvate thereof.

Suitable values for $Q_1$ include halogen, such as chloro or bromo, preferably chloro.

The reaction (i) of a compound of formula (VI) with $R_1'R_2'NCOQ_1$ may either take place in an inert solvent, such as xylene or higher boiling solvent or, more preferably in neat $R_1'R_2'NCOQ_1$ at high temperature, for example 140°–190° C., preferably 165°–170° C.

Suitable values for the alkyl group in (ii) (a) include methyl, ethyl, n- and iso-propyl. Preferably the alkyl group is methyl or ethyl. Suitable alkylating agents include dialkylsulphate, alkyl iodide or trialkyloxonium tetrafluoroborate. The reaction is preferably carried out in an inert solvent such as dichloromethane and the alkylating agent is preferably triethyloxonium tetrafluoroborate. The reaction proceeds through an intermediate of formula (VIIa) or a salt thereof:

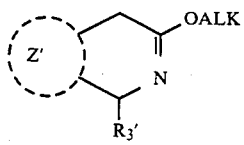

(VIIa)

wherein Alk is an alkyl group and the remaining variables are as defined in formula (VI). The intermediate of formula (VIIa) is the tetrafluoroborate salt when the alkylating agent is a trialkyloxonium tetrafluoroborate.

$HNR_1'R_2'$ may then be added to the compound of formula (VIIa), without isolation, and the compound of formula (I) extracted by conventional methods. Alternatively, the compound of formula (VIIa) may be isolated, and, for example, converted to a salt, such as its hydrochloride salt, before reaction with $HNR_1'R_2'$.

Suitable halogenating agents in (ii)b) include phosgene or phosphorous oxychloride. The reaction proceeds through an intermediate of formula (VIIb):

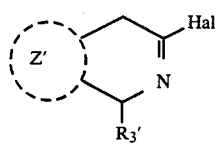

(VIIb)

wherein Hal is a halogen atom, in particular chlorine, and the remaining variables are as defined for formula (VI).

The intermediate of formula (VIIb) may then be reacted with $HNR_1'R_2'$, with or without prior isolation of the intermediate. If isolated, the intermediate may be converted to a salt, for example its hydrochloride, before reaction.

It will be appreciated that a compound of formula (Ia) may be converted to a compound of formula (I), or one compound of formula (I) may be converted to another compound of formula (I), by interconversion of suitable substituents. Thus certain compounds of formula (I) and (Ia) are useful intermediates in forming other compounds of the present invention.

$R_1'$ and $R_2'$ may be alkyl or acyl groups and converted to $R_1/R_2$ hydrogen atoms by conventional amine dealkylation or deacylation. When $R_1'$ or $R_2'$ is benzyl or substituted benzyl it may be converted to an $R_1$ or $R_2$ hydrogen atom by catalytic hydrogenation or other method of reduction. $R_1'$ and $R_2'$ as hydrogen atoms may be converted to $R_1$ and $R_2$ alkyl groups by conventional amine alkylation, or by acylation followed by reduction. $R_1'$ and $R_2'$ are preferably $R_1$ and $R_2$ respectively.

Conversions of substituents on an aromatic group $R_3'$ or Z' to obtain $R_3$ or Z are generally known in the art of aromatic chemistry. For example, a nitro substituent may be converted to an amino group by conventional catalytic hydrogenation. $R_3'$ is preferably $R_3$. Z' is preferably Z.

Such conversions may take place in any desired or necessary order. They may be performed before reactions (i) or (ii) so that $R_1$, $R_2'$, $R_3'$, and Z' are $R_1$, $R_2$, $R_3$ and Z, or after those reactions.

The compounds of formula (I) may be converted into their pharmaceutically acceptable acid addition salts by reaction with the appropriate organic or mineral acids.

Also salts or solvates of the compounds of formula (I) which are not pharmaceutically acceptable may be useful as intermediates in the production of pharmaceutically acceptable salts or solvates. Accordingly such salts or solvates also form part of this invention.

Compounds of formula (VI) may be prepared by the method described in Acta Chimica Academide Scientiarum Hungaricae 1969, 60(1-2), 177 and 1981, 108, 255, that is by reaction of a compound of formula (VIII):

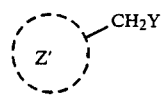

(VIII)

where Y is CN or $CONH_2$
with an aldehyde of formula (IX):

$R_3'CHO$ (IX)

in polyphosphoric acid at a temperature of 100° to 140° C. The reaction is preferably carried out in polyphosphoric acid containing 82 to 84% of phosphorus pentoxide and preferably at 100° to 140° C., without using any other solvent. The reaction takes place generally within 1 to 12 hours.

As mentioned previously, the compounds of formula (I) exist in more than one stereoisomeric form and the processes of the invention produces mixtures thereof. The individual isomers may be separated one from another by resolution using an optically active acid such as tartaric acid. Alternatively, an asymmetric synthesis would offer a route to the individual form. Intermediates of formula (VI) together with the described processes for their preparation, form an aspect of the invention.

More particularly the present invention provides as novel compounds a compound of formula (X):

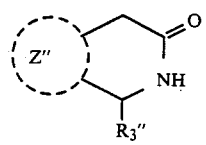

(X)

where $R_3''$ and Z'' are $R_3$ and Z as defined for formula (I) with the proviso that Z'' is not unsubstituted phenyl when $R_3''$ is pyridyl.

The present invention further provides a pharmaceutical composition, which comprises a compound of formula (I) or a pharmaceutically acceptable salt or solvate thereof and a pharmaceutically acceptable carrier.

A composition of this invention is useful in the treatment of rheumatism and arthritis and in the treatment of pain and other inflammatory conditions and also in the treatment of and prophylaxis of bronchial asthma, rhinitis, hay fever and allergic eczema.

A composition of the invention, which may be prepared by admixture, may contain a diluent, binder, filler, disintegrant, flavouring agent, colouring agent, lubricant, preservative in conventional manner. These conventional excipients may be employed in conventional manner, for example as in the preparation of compositions of ketoprofen, indomethacin, naproxen, acetylsalicyclic acid and other analgesic or anti-inflammatory agents.

A composition of the invention may be adapted for oral, topical, rectal or parenteral—intravenous or intramuscular—administration but oral administration is preferred.

A composition of the invention will preferably be in the form of a unit dose, such as a tablet or capsule or a sachet containing reconstitutable powder. A unit dose for inflammatory diseases will generally contain from 20 to 1000 mg and preferably will contain from 30 to 500 mg, in particular 50, 100, 150, 200, 250, 300, 350, 400, 450 or 500 mg. The composition may be administered once or more times a day, for example 2, 3 or 4 times daily, so that the total daily dose for a 70 kg adult will normally be in the range 100 to 3000 mg. Alternatively the unit dose will contain from 2 to 20 mg of a compound of the invention and be administered in multiples, if desired, to give the preceding daily dose.

For use in the treatment or prophylaxis of allergic disorders, in any of the preceding formulations, a suitable dosage unit may contain 0.01 to 500 mg of active ingredient, more suitably 1 to 500 mg for use via the oral route, 0.01 to 10 mg via inhalation, which is preferred. The effective dose of compound depends on the particular compound employed, the condition of the patient and the frequency and route of administration, but in general is in the range of from 0.001 mg/day to 100 mg/day per kilogram of the patient's body weight.

Where appropriate, small amounts of other antiasthmatics and bronchodilators, for example sympathomimetic amines such as isoprenaline, isoetharine, salbutamol, phenylephrine and ephedrine; xanthine derivatives such as theophylline and aminophylline and corticosteroids such as prednisolone and adrenal stimulants such as ACTH may be included.

A particular composition of the invention for inflammatory diseases is a hard gelatin capsule containing the required amount of a compound of the invention in the form of a powder or granulate in intimate mixture with a lubricant, such as magnesium stearate, a filler, such as microcrystalline cellulose, and a disintegrant, such as sodium starch glycollate.

Preparations especially suitable for administration to the respiratory tract include, for example, a snuff, an aerosol, a solution for a nebulizer, or a microfine powder for insufflation, alone or in combination with an inert carrier such as lactose. In such a case the particles of active compound suitably have diameters of less than 50 microns, preferably less than 10 microns.

For topical administration, the preparations may also be presented as an ointment, cream, lotion, gel, aerosol, or skin paint for topical application.

The present invention additionally provides a method of treating an inflammatory and/or a painful condition such as rheumatism and/or allergic conditions in mammals, such as humans, which comprises administering an effective amount of a compound, pharmaceutically acceptable salt or solvate, or composition of the invention to the mammal.

The present invention also provides a compound, pharmaceutically acceptable salt or solvate, or composition of the invention for use in the treatment of inflammatory and/or painful conditions, such as rheumatism, and/or allergic conditions in mammals.

The following Descriptions and Examples illustrate the preparation of compounds of the invention (all temperatures are in °C.). The subsequent pharmacological data illustrates their activity.

DESCRIPTION 1

1-[1'-(4'-Chloronaphthyl)]-1,4-dihydroisoquinol-3-one

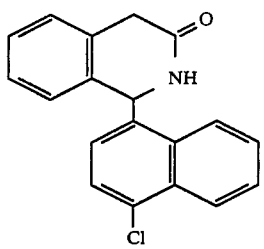

This material was prepared in a similar manner to that described in Acta Chimica Academiae Scientiarum Hungaricae 1969, 60(1-2), 177. Thus a mixture of benzyl cyanide (5 g, 40 mmol.) and polyphosphoric acid (25 g) was heated and stirred at 80° C. for 45 mins. 4-Chloronaphthaldehyde (3.8 g, 20 mmol) was added with vigorous stirring over 25 mins. The mixture was heated to 135° C. for 3 h, cooled to 100° C. and poured into water (50 ml). 0.88 Ammonium hydroxide (100 ml) was added and the mixture left overnight. The precipitate was filtered off and refluxed in 5% sodium hydroxide (80 ml). The mixture was filtered hot after 2 h and the solid recrystallised from ethyl acetate to give [1'-(4'-chloronaphthyl)]-1,4-dihydroisoquinol-3-one (1.6 g, 27%) m.p. 180°-183° C.

Analysis: $C_{19}H_{14}NOCl$ requires C, 74.15; H, 4.59; N, 4.55; Cl, 11.53. Found: C, 73.99; H, 4.43; N, 4.49; Cl, 11.87%.

DESCRIPTION 2

1-[2'-(1'-Chloronaphthyl)]-1,4-dihydroisoquinol-3-one hemihydrate

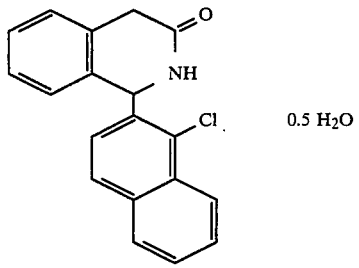

This compound was prepared in the usual manner from benzyl cyanide and 1-chloro-2-naphthaldehyde. m.p. 195°-197° C. (ethanol/ethyl acetate).

Analysis: $C_{19}H_{14}NOCl$ $0.5H_2O$ requires C, 72.04; H, 4.77; N, 4.42; Cl 11.19. Found: C, 71.99; H, 4.61; N, 4.18; Cl, 11.09%.

DESCRIPTION 3

5-Chloro-1-(2'-chlorophenyl)-1,4-dihydrobenz[g]isoquinol-3-one

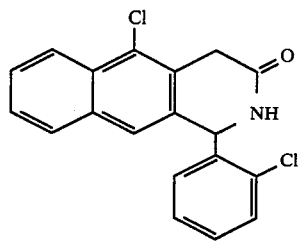

This material was prepared in a similar manner to that described in *Acta Chimica Academie Scientarum Hungaricae*, Tomus 108(3), 255, (1981). Thus a mixture of 1-chloro-2-naphthylacetonitrile (25 g) and polyphosphoric acid (100 g) was heated and stirred at 80° for 30 min. 2-Chlorobenzaldehyde (8.7 g) was added with stirring over 30 min. The mixture was heated at 130° C. for 3 hours, cooled and poured into water. 0.88 Ammonium hydroxide was added and the mixture left overnight. The precipitate was filtered off and refluxed in 5% sodium hydroxide. The mixture was filtered hot after 2 hours and the product chromatographed (silica gel, chloroform as eluant) to give 5-chloro-1-(2'-chlorophenyl)-1,4-dihydrobenzo[g]isoquinol-3-one (5.3 g) m.p. 252°–254° C.

NMR (d$_6$-DMSO) δ 3.95 (s, 2H) 6.30 (broad s, 1H) 7.30–8.90 (m, 9H).

H.R.M.S. (m/z) C$_{19}$H$_{13}$NCl$_2$O requires 341.0374, found 341.0371.

Unless otherwise stated, Descriptions 4–20 were prepared by the method of Description 3.

DESCRIPTION 4

5-Bromo-1-(2'-chlorophenyl)-1,4-dihydro-benz[g]isoquinol-3-one

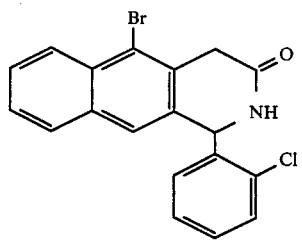

This compound was prepared from 1-bromo-2-naphthylacetonitrile and 2-chlorobenzaldehyde. m.p. 256°–257° C. (chloroform-ethyl acetate).

H.R.M.S. (m/z) C$_{19}$H$_{13}$NOClBr requires 386.9848; found 386.9845.

DESCRIPTION 5

1-(2'-Chlorophenyl)-1,4-dihydro-benz[g]isoquinol-3-one

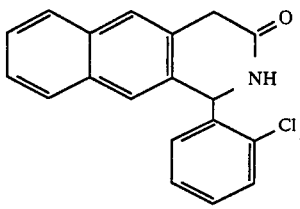

A mixture of 5-bromo-1-(2'-chlorophenyl)-1,4-dihydrobenz[g]isoquinol-3-one (Description 7) (7.6 g), sodium acetate (3.0 g) and 10% palladium-charcoal (2.0 g) in acetic acid (750 ml) was hydrogenated at atmospheric temperature and pressure until the initial rapid uptake of hydrogen had ceased (2.5 hours). The mixture was filtered (celite) and the filtrate evaporated to dryness in vacuo and recrystallised from ethylacetate to afford the title compound (4.65 g) m.p. 234°–237° C.

Analysis: C$_{19}$H$_{14}$NOCl requires C, 74.15; H, 4.58; N, 4.55; Cl, 11.52%: Found C, 74.24; H, 4.58; N, 4.42; Cl, 11.62%.

DESCRIPTION 6

5-Chloro-1-(2'-fluorophenyl)-1,4-dihydro-benz[g]isoquinol-3-one

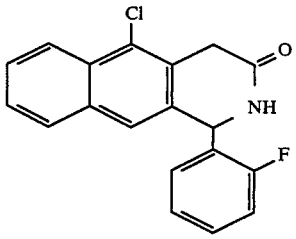

From 1-chloro-2-naphthylacetonitrile and 2-fluorobenzaldehyde, m.p. 206°–9° (ethanol).

Analysis: C$_{19}$H$_{12}$NOClF requires C, 70.27; H, 3.72; N, 4.31%: found C, 70.19; H, 4.06; N, 4.08%.

DESCRIPTION 7

5-Bromo-1-(2'-fluorophenyl)-1,4-dihydro-benz[g]isoquinol-3-one

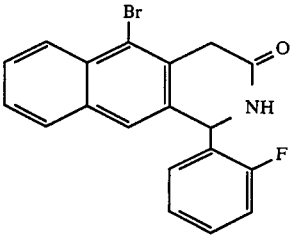

From 1-bromo-2-naphthylacetonitrile and 2-fluorobenzaldehyde. m.p. 215–18 (chloroform).

N.M.R. (d$^6$-DMSO) δ 3.90 (2H, s) 6.20 (1H, b) 7.00–8.50 (9H, m) 8.70 (1H, b).

DESCRIPTION 8

1-(2'-Fluorophenyl)-1,4-dihydro-benz[g]isoquinol-3-one

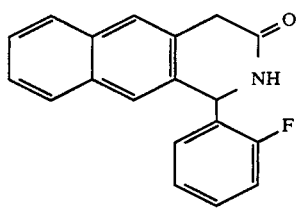

Prepared from 5-bromo-1-(2'-fluorophenyl)-1,4-dihydrobenz[g]isoquinol-3-one (Description 7) by hydrogenation over palladium-charcoal as described for Description 5.

m.p. 245°–250° C. (ethanol).

DESCRIPTION 9

4-(2'-Fluorophenyl)-1,4-dihydro-benz[f]isoquinol-2-one

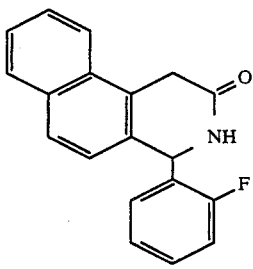

This compound was prepared from naphthalene-1-acetonitrile and 2-fluorobenzaldehyde by the method described for Description 1. m.p. 259°–261° C. (chloroform).

Analysis: $C_{19}H_{14}NOF$ requires C, 78.33; H, 4.88; N, 4.80%: found C, 78.38; H, 4.90; N, 4.88%.

DESCRIPTION 10

1-(2'-Fluorophenyl)-1,4-dihydro-benz[h]isoquinol-3-one

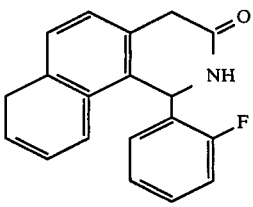

From naphthalene-2-acetonitrile and 2-fluorobenzaldehyde. m.p. 265°–8° (ethanol).

N.M.R. (d6-DMSO) δ 3.80 (2H, q) 6.50 (1H, b) 7.00–8.30 (10H, m), 8.70 (1H, b).

H.R.M.S. (m/z) $C_{19}H_{14}NOF$ requires 291.1059, found 291.1073.

Analysis: $C_{19}H_{14}NOF$ requires C, 78.30; H, 4.84; N, 4.81%: found C, 77.90; H, 4.80; N, 4.59%.

DESCRIPTION 11

6-Fluoro-4-(2'-chlorophenyl)-1,4-dihydro-benz[f]isoquinol-2-one

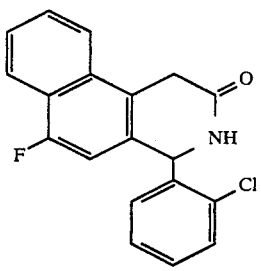

Prepared from 4-fluoro-naphthalene-1-acetonitrile and 2-chlorobenzaldehyde.

DESCRIPTION 12

6-Bromo-4-(2'-fluorophenyl)-1,4-dihydro-benz[f]isoquinol-2-one

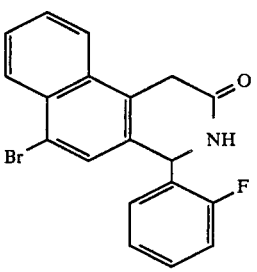

Prepared from 4-bromo-1-naphthylacetonitrile and 2-fluorobenzaldehyde. m.p. 257°–260° C.

N.M.R. (d6-DMSO) δ4.00 (2H, s) 6.07 (1H, broad s) 7.10–8.30 (9H, m) 8.65 (1H, d).

H.R.M.S. (m/z) $C_{19}H_{13}ONFBr$ requires 369.0186. found 369.0165.

DESCRIPTION 13

1-(2'-Fluorophenyl)-8-methoxy-1,4-dihydro-benz[h]isoquinol-3-one

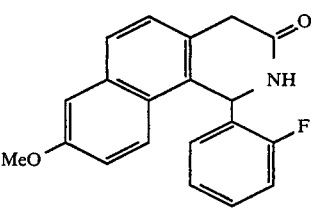

Prepared from 6-methoxy-2-naphthylacetamide and 2-fluorobenzaldehyde.

DESCRIPTION 14

1-(2'-Fluorophenyl)-5-methoxy-1,4-dihydro-benz[g]isoquinol-3-one

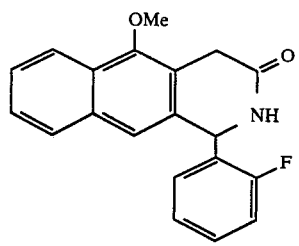

Prepared from 1-methoxy-2-naphthylacetonitrile and 2-fluorobenzaldehyde.

DESCRIPTION 15

1-(2'-Chloro-4'-pyridyl)-1,4-dihydro-isoquinol-3-one

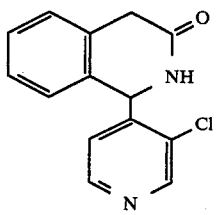

Prepared from benzylnitrile and 2-chloro-4-pyridine carboxaldehyde[1] (prepared by the method described in Tetrahedron Letters, 1980, 21, 4137).

[1] R. B. Moffet, A. Roberts, E. L. Schumann, L. A. Paquitte. J. Het. Chem., 1979, 16 (6), 1459.

N.M.R. (CDCl$_3$) δ3.67 (s, 2H) 6.12 (s, 1H) 6.90 (d, 1H) 7.28 (s, 4H) 8.42 (d, 1H) 8.67 (s, 1H).

DESCRIPTION 16

6-Fluoro-1-(3'-pyridyl)-1,4-dihydro-isoquinol-3-one

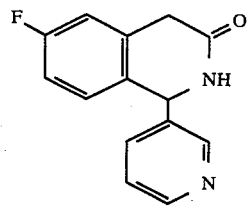

Prepared from 3-fluorophenylacetamide and pyridine-3-carboxaldehyde. m.p. 183°-184° C. (ethanol).

Analysis: $C_{14}H_{11}N_2OF$ requires C, 69.41; H, 4.58; N, 11.56; found C, 69.39; H, 4.53; N, 11.62%.

DESCRIPTION 17

5-Chloro-1-(3'-pyridyl)-1,4-dihydro-isoquinol-3-one

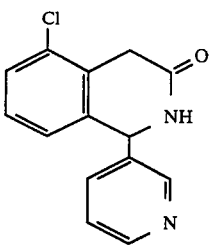

Prepared from 2-chloro-phenylacetonitrile and pyridine-3-carboxaldehyde. m.p. 182°-185° (ethyl acetate).

DESCRIPTION 18

5-Bromo-8-methoxy-1-(3'-pyridyl)-1,4-dihydroisoquinol-3-one

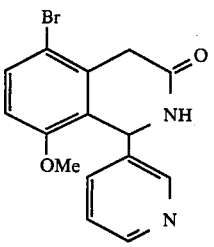

Prepared from 2-bromo-5-methoxyphenylacetamide and pyridine-3-carboxaldehyde. m.p. 265°-267° C. (ethanol).

DESCRIPTION 19

8-Methoxy-1-(3'-pyridyl)-1,4-dihydroisoquinol-3-one

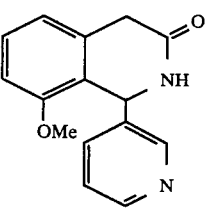

Prepared from 5-bromo-8-methoxy-1-(3'-pyridyl)-1,4-dihydroisoquinol-3-one (Description 18) by the method of Description 5.

DESCRIPTION 20

6-Methoxy-1-(3'-pyridyl)-1,4-dihydroisoquinol-3-one

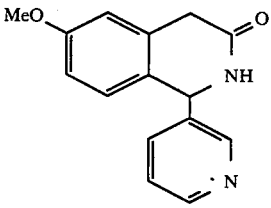

Prepared from 3-methoxyphenylacetamide and pyridine-3-carboxaldehyde.

EXAMPLE 1

1-[1'-(4'-Chloronaphthyl)]-3-dimethylamino-1,4-dihydroisoquinoline hydrochloride hydrate

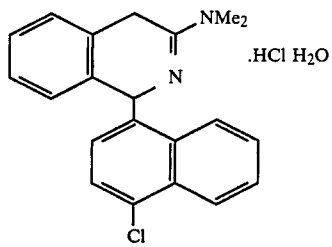

1-[1'-(4'-Chloronaphthyl)]-1,4-dihydroisoquinol-3-one (1.6 g, 5.4 mmol) was dissolved in dimethylcarbamyl chloride (5.4 ml) on an oil bath (bath temperature 160°–170° C.) for 2 h. The mixture was cooled, evaporated under reduced pressure and partitioned between water (15 ml), 5M hydrochloric acid, ethyl acetate (10 ml) and chloroform (10 ml). The organic layer was separated and extracted with a portion of water (10 ml). The combined aqueous extracts were washed with ethyl acetate (3×10 ml) and basified with 10% sodium hydroxide. The oil so formed was extracted with ethyl acetate (2×50 ml) and the combined ethyl acetate layers were washed with brine (25 ml) and dried over sodium sulphate. The solution was filtered and reduced to 50 ml under reduced pressure. Ethereal hydrogen chloride was added to precipitate the salt which was recrystallised from ethyl acetate to give 1-[1'-(4'-chloronaphthyl)]-3-dimethylamino-1,4-dihydroisoquinoline hydrochloride (0.8 g, 40%) m.p. 81°–82° C.

Analysis: $C_{21}H_{20}N_2Cl_2.H_2O$ requires C, 64.78; H, 5.69; N, 7.19; Cl, 18.21. Found: C, 64.42; H, 5.56; N, 7.11; Cl, 18.57%.

EXAMPLE 2

1-[2'-(1'-Chloronaphthyl)]-3-dimethylamino-1,4-dihydroisoquinoline hydrochloride

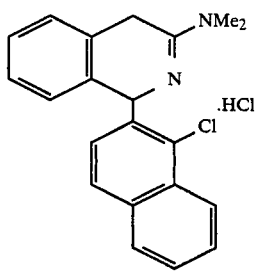

This compound was prepared from 1-[2'-(1'-chloronaphthyl)]-1,4-dihydroisoquinol-3-one in the usual manner m.p. 248°–250° C. (ethanol/ethyl acetate).

EXAMPLE 3

5-Chloro-1-(2'-chlorophenyl)-3-dimethylamino-1,4-dihydro-benz[g]isoquinoline hydrochloride hemihydrate

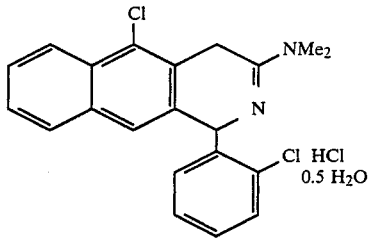

5-Chloro-1-(2'-chlorophenyl)-1,4-dihydro-benz[g]isoquinol-3-one (Description 3) (4.5 g) was dissolved in dimethylcarbamyl chloride (25 ml) on an oil bath (bath temperature 160°–170° C. ) for 2 h. The mixture was cooled, evaporated under reduced pressure and partitioned between water (50 ml), 5M hydrochloric acid, ethyl acetate (25 ml) and chloroform (25 ml). The organic layer was separated and extracted with water (25 ml). The combined aqueous extracts were washed with ethyl acetate (2×25 ml) and basified with 10% sodium hydroxide solution. The oil so formed was extracted with ethyl acetate (2×100 ml) and the combined organic extracts dried over sodium sulphate. The solution was filtered and reduced to 100 ml under reduced pressure. Ethereal hydrogen chloride was added to precipitate the salt to give 5-Chloro-1-(2'-chlorophenyl)-3-dimethylamino-1,4-dihydro-benz[g]isoquinoline hydrochloride hemihydrate (0.85 g) m.p. 232°–234° C.

N.M.R. (d$_6$-DMSO) δ3.25 (s, 6H) 4.47 (q, 2H) 6.50 (s, 1H) 7.30–8.25 (m, 9H).

Analysis: $C_{21}H_{19}N_2Cl_3.0.5H_2O$ requires C, 60.81; H, 4.86; N, 6.75%: found C, 61.04; H, 4.51; N, 6.59%.

H.R.M.S. (m/z) $C_{21}H_{18}N_2Cl_2$ requires 368.0848: found 368.0880.

Unless otherwise stated, Examples 4–21 were prepared by the method described in Examples 1 and 3

EXAMPLE 4

5-Bromo-1-(2'-chlorophenyl)-3-dimethylamino-1,4-dihydro-benz[g]isoquinoline hydrochloride

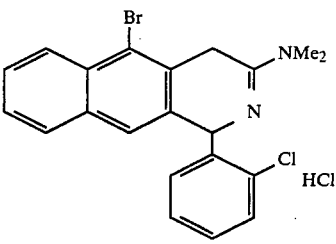

This compound was prepared from 5-bromo-1-(2'-chlorophenyl)-1,4-dihydro-benz[g]isoquinol-3-one (Description 4). m.p. 176°–179° C. (dichloroethane-ethyl acetate) H.R.M.S. (m/z) $C_{21}H_{18}N_2BrCl$ requires 412.0341; found 412.0349.

EXAMPLE 5

1-(2'-chlorophenyl)-3-dimethylamino-1,4-dihydro-benz[g]isoquinoline hydrochloride hydrate (1.5)

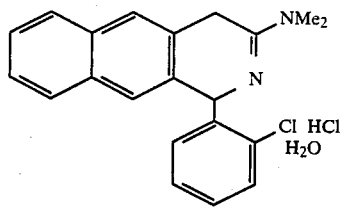

From 1-(2'-chlorophenyl)-1,4-dihydro-benz[g]isoquinol-3-one. m.p. 251°-2° (chloroform/dichloroethane/ethylacetate).

N.M.R. (CDCl$_3$) 3.50 (6H, b) δ4.30 (2H, q), 6.60 (1H, s) 7.00–8.20 (10H, m) 11.70 (1H, b exchanges with D$_2$O).

Analysis C$_{21}$H$_{19}$N$_2$Cl.HCl1.5H$_2$O requires C, 63.32; H, 5.82; N, 7.03%: found C, 63.28; H, 5.78; N, 6.87%.

EXAMPLE 6

5-Chloro-1-(2'-fluorophenyl)-3-dimethylamino-1,4-dihydro-benz[g]isoquinoline hydrochloride hydrate (3.0)

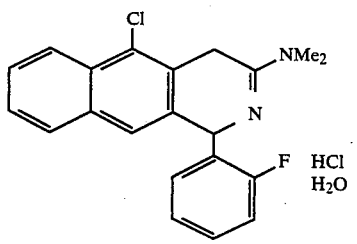

From 5-chloro-(2'-fluorophenyl)-1,4-dihydro-benz[g]isoquinol-3-one. m.p. 172°-5° (Diethylether/Ethyl Acetate).

N.M.R. (CDCl$_3$) δ 3.50 and 3.60 (6H, 2×s) 4.20 (2H, q), 6.60 (1H, m) 6.70–8.40 (9H, m) 11.00 (1H, b exchanges with D$_2$O).

H.R.M.S. (m/z) C$_{21}$H$_{18}$N$_2$FCl requires 352.1143, found 352.1144.

Analysis C$_{21}$H$_{18}$N$_2$ClF.HCl 3H$_2$O requires C, 56.89; H, 5.68; N, 6.32%: found C, 56.78; H, 5.44; N 6.64%.

EXAMPLE 7

5-Bromo-1-(2'-fluorophenyl)-3-dimethylamino-1,4-dihydro-benz[g]isoquinoline hydrochloride

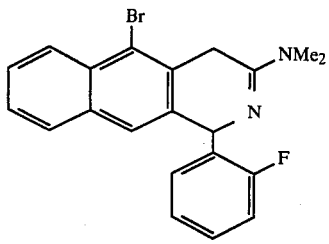

From 5-bromo-(2'-fluorophenyl)-1,4-dihydro-benz[g]isoquinol-3-one (Description 7). H.R.M.S. (m/z) C$_{21}$H$_{18}$N$_2$Br(81)F requires 398.0617; found 398.0639.

EXAMPLE 8

1-(2'-Fluorophenyl)-3-dimethylamino-1,4-dihydro-benz[g]isoquinoline hydrochloride

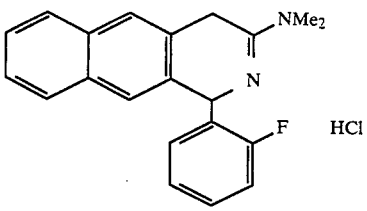

Prepared from 1-(2'-fluorophenyl)-1,4-dihydro-benz[g]isoquinol-3-one (Description 8).

m.p. 225°–228° C. (dichloroethane/toluene).

N.M.R. (CDCl$_3$/DMSO) δ 3.5, 3.6 (2×3H, 2×s) 4.3 (2H, m) 6.1 (1H, b) 6.8–8.0 (10H, m).

EXAMPLE 9

4-(2'-Fluorophenyl)-2-dimethylamino-1,4-dihydro-benz[f]isoquinoline hydrochloride hemihydrate

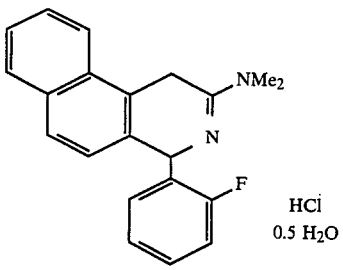

This compound was prepared from 4-(2'-fluorophenyl)-1,4-dihydro-benz[f]isoquinol-2-one (Description 9). m.p. 246°–250° C. (dichloroethane-ethylacetate).

Analysis: C$_{21}$H$_{19}$N$_2$F.HCl0.5H$_2$O requires C, 69.32; H, 5.82; N, 7.70; Cl, 9.74%; found C, 69.65; H, 5.44; N, 7.59; Cl, 9.87%.

EXAMPLE 9A 4-(2'-chlorophenyl)-2-dimethylamino-1,4-dihydrobenz[f]isoquinoline hydrochloride was prepared by analogous procedures to those of Description 9 and Example 9.

EXAMPLE 10

1-(2'-Fluorophenyl)-3-dimethylamino-1,4-dihydro-benz[h]isoquinoline hydrochloride hydrate (1.5)

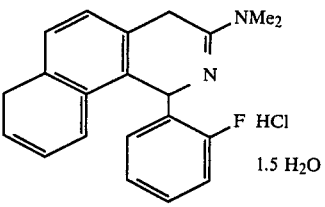

From 1-(2'-fluorophenyl)-1,4-dihydro-benz[h]isoquinol-3-one (Description 10). m.p. 174°-7° (chloroform/ethyl acetate).

Analysis: $C_{21}H_{19}N_2F.HCl$ $1.5H_2O$ requires C, 66.05; H, 6.07; N, 7.33%: found C, 65.73; H, 6.08; N, 7.26%.

EXAMPLE 11

6-Fluoro-4-(2'-chlorophenyl)-2-dimethylamino-1,4-dihydro-benz-[f]isoquinoline hydrochloride

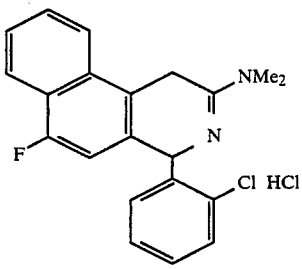

Prepared from 6-fluoro-4-(2'-chlorophenyl)-1,4-dihydrobenz[f]-isoquinol-2-one (Description 11). m.p. 238°–242° C.

EXAMPLE 12

6-Bromo-4-(2'-fluorophenyl)-2-dimethylamino-1,4-dihydro-benz[f]isoquinoline hydrochloride hydrate

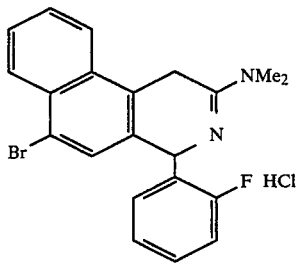

Prepared from 6-bromo-4-(2'-fluorophenyl)-1,4-dihydrobenz[f]isoquinol-2-one (Description 12).
m.p. 247°–250° C.
N.M.R. ($d_6$-DMSO) δ 3.30, 3.55 (2×3H, 2×s) 4.65 (2H, s) 6.40 (1H, broad s) 7.10, 8.50 (9H, m).

EXAMPLE 13

1-(2'-Fluorophenyl)-3-dimethylamino-8-methoxy-1,4-dihydro-benz[h]isoquinoline hydrochloride

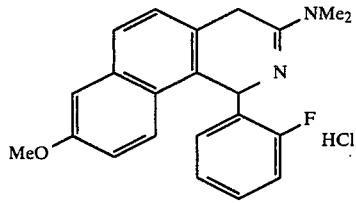

Prepared from 1-(2'-fluorophenyl)-8-methoxy-1,4-dihydro-benz[h]isoquinol-3-one (Description 13).

EXAMPLE 14

1-(2'-Fluorophenyl)-3-dimethylamino-5-methoxy-1,4-dihydro-benz[g]isoquinoline hydrochloride

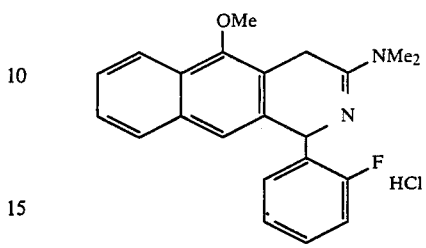

Prepared from 1-(2'-fluorophenyl)-5-methoxy-1,4-dihydro-benz[g]isoquinol-3-one (Description 14).

EXAMPLE 15

1-(3'-pyridyl)-3-dimethylamino-1,4-dihydro-isoquinoline dihydrochloride hydrate

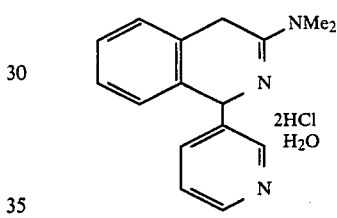

1-(3'-Pyridyl)-1,4-dihydroisoquinol-3-one (9 g) [prepared as in Acta Chimica Academiae Scientarum Hungaricae, 102(3), 305 (1979)] was dissolved in dimethylcarbamyl chloride (50 ml) and the solution heated on an oil bath (bath temperature 165°) for one and three quarter hours. The solution was cooled and evaporated. The residue was partitioned between chloroform (200 ml) and 10% aqueous sodium carbonate. The chloroform layer was dried over sodium sulphate and evaporated under reduced pressure. The residue was chromatographed on neutral alumina (200 g) deactivated with water 3% (w/w) using chloroform as eluent. Treatment of the desired fractions with ethereal hydrogen chloride followed by evaporation under reduced pressure gave 1-(3'-pyridyl)-3-dimethylamino-1,4-dihydro-isoquinoline dihydrochloride hydrate. m.p. 210°–18°.

Analysis: $C_{16}H_{17}N_3.2HCl.H_2O$ requires C, 56.15; H, 6.18; N, 12.28%: found C, 56.24; H, 5.91; N, 11.88%.

EXAMPLE 15A 1-(3'-pyridyl)-3-dimethylamino-1,4-dihydro-benz[f]isoquinoline dihydrochloride was prepared by procedures analogous to those of Example 15.

Similarly prepared was

EXAMPLE 16

1-(2'-Chloro-4'-pyridyl)-3-dimethylamino-1,4-dihydroisoquinoline dihydrochloride

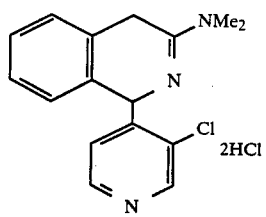

From 1-(2'-chloro-4'-pyridyl)-1,4-dihydro-isoquinol-3-one (Description 15). Ammonia Chemical Ionisation 286 (M+1 for free base). H.R.M.S. (m/z) $C_{16}H_{16}N_3\phi Cl$ requires 285.1033; found 285.1014.

EXAMPLE 17

5-Chloro-1-(3'-pyridyl)-3-dimethylamino-1,4-dihydroisoquinoline dihydrochloride

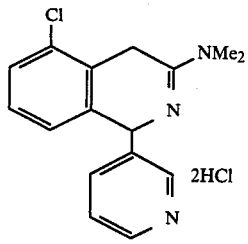

Prepared from 5-chloro-1-(3'-pyridyl)-1,4-dihydroisoquinol-3-one (Description 17). m.p. 245°–252° C. (chloroform).

EXAMPLE 18

6-Fluoro-1-(3'-pyridyl)-3-dimethylamino-1,4-dihydroisoquinoline dihydrochloride

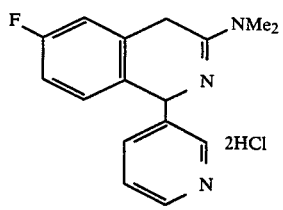

Prepared from 6-fluoro-1-(3'-pyridyl)-1,4-dihydroisoquinol-3-one (Description 16) (7.5 g) and dimethylcarbamoyl chloride in the usual manner. The reaction mixture was filtered (hot) and the filtrate was evaporated to dryness in vacuo. The residue was dissolved in water (50 ml) and 5N-hydrochloride acid (20 ml). The aqueous solution was basified with an excess of sodium bicarbonate solution and extracted (3×) with ethyl acetate. The aqueous layer was now basified with an excess of sodium carbonate solution and re-extracted (2×) with ethyl acetate. This organic layer which contained amidino-product, was washed with water and dried (Na₂SO₄). Evaporation to dryness in vacuo afforded the free base of Example 18 which was dissolved in chloroform and treated with an excess of ethereal hydrogen chloride. Evaporation to dryness in vacuo afford the compound of Example 18 as a very hygroscopic pale brown foam (1.4 g), m.p. 120°–125° C. Recrystallization from chloroform increased the melting point to 212°–220° C.

EXAMPLE 19

5-Bromo-3-dimethylamino-8-methoxy-1-(3'-pyridyl)-1,4-dihydroisoquinoline dihydrochloride

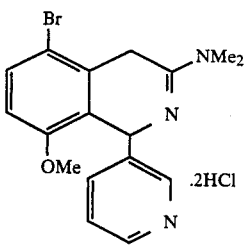

Prepared from 5-bromo-3-dimethylamino-8-methoxy-1-(3'-pyridyl)-1,4-dihydroisoquinol-3-one (Description 18). m.p. 220°–245° C.

EXAMPLE 20

3-Dimethylamino-8-methoxy-1-(3'-pyridyl)-1,4-dihydroisoquinoline dihydrochloride

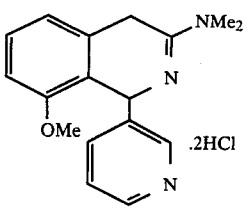

Prepared from 3-dimethylamino-8-methoxy-1-(3'-pyridyl)-1,4-dihydroisoquinol-3-one (Description 19).

EXAMPLE 21

3-Dimethylamino-6-methoxy-1-(3'-pyridyl)-1,4-dihydroisoquinoline dihydrochloride

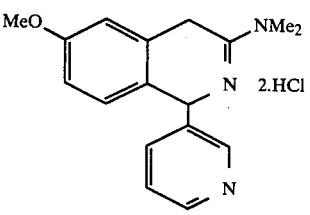

Prepared from 3-dimethylamino-6-methoxy-1-(3'-pyridyl)-1,4-dihydroisoquinol-3-one (Description 20).

EXAMPLE 22

5-Bromo-3-dimethylamino-8-hydroxy-1-(3'-pyridyl)-1,4-dihydroisoquinoline dihydrobromide

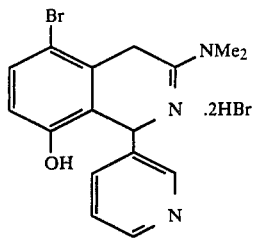

Prepared from 5-bromo-3-dimethylamino-8-methoxy-1-(3'-pyridyl)-1,4-dihydroisoquinoline dihydrochloride (Example 19) by heating in 48 percent aqueous HBr.

EXAMPLE 23

3-Dimethylamino-8-hydroxy-1-(3'-pyridyl)-1,4-dihydroisoquinoline dihydrobromide

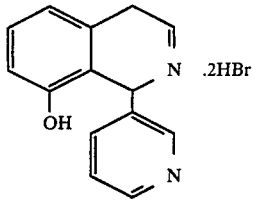

Prepared from 3-dimethylamino-8-methoxy-1-(3'-pyridyl)-1,4-dihydroisoquinoline dihydrochloride (Example 20) by heating in 48 percent aqueous HBr.

EXAMPLE 24

3-Dimethylamino-6-hydroxy-1-(3'-pyridyl)-1,4-dihydroisoquinoline dihydrobromide

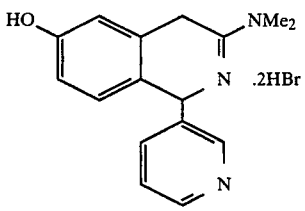

Prepared from 3-dimethylamino-6-methoxy-1-(3'-pyridyl)-1,4-dihydroisoquinoline dihydrochloride (Example 21) by heating in 48 percent aqueous HBr.

Biological Activity

The potential therapeutic activity of compounds of this invention may be demonstrated by in vivo and in vitro disease models as follows:

ADJUVANT ARTHRITIS TEST IN THE RAT

The test is as described by Newbould, Brit. J. Pharmacol., 1963, 21, 127–136. Compounds were active at the doses shown below.

|  | Dose (mg/kg p.o.) |
| --- | --- |
| Example 1 | 22 |
| Example 3 | 19 |

CARRAGEENIN-INDUCED PLEURISY IN THE RAT

This model of monocyte accumulation is based on the method of R. Vinegar, J. F. Truax, J. L. Selph and F. A. Voelker [Federation Proceedings 41, 2588–2595, 1982].

0.2 ml of a 2.0% solution of λ-carrageenin (Viscarin 402) in saline was injected intrapleurally in anaesthetised rats (wt. approx. 175–200 g). Compounds were administered 1 hour before carrageenin and at 24 and 48 hours after carrageenin. 72 hours after carrageenin injection, 4.0 ml of EDTA solution (5 g EDTA in 100 ml of 0.9% saline and 325 mg phenol red added together with saline to 1 liter) was injected intrapleurally after killing the animals, and the exudate removed with a syringe through the diaphragm. Exudate volume was calculated from the dilution of the phenol red injected, determined spectrophotometrically (560 nm) and cellular content estimated with a DNA assay [Karsten U. and Wollenberger A. Anal. Biochem. 77, 464–470, 1977].

Compounds were active at the doses shown below:

|  | Dose (mg/kg p.o.) |
| --- | --- |
| Example 15 | 3 |
| Example 3 | 25 |

Interleukin I stimulation of collagenase release in vitro

Interleukin 1 (IL1) is known to have effects on a wide range of cell types; e.g. the stimulation of enzyme release from synovial cells in vitro. This property potentially makes IL1 of importance in those conditions where connective tissue destruction occurs. Recently, the discovery of IL1-like activity from the joint effusions from a wide range of arthritides (Wood, Ihrie, Dinarello and Cohen, Arthritis and Rheumatism, 26, 975–983 (1983)), implies its involvement in those diseases. Any drug which could abrogate IL1's potentiation of enzyme release by synovial cells in vivo could be of clinical benefit in inflammatory diseases such as rheumatoid arthritis.

For testing, synovial cells are derived from rabbit knees and grown in vitro. Monocyte conditioning factor (MCF), otherwise known as Interleukin 1, is obtained from glycogen-elicited rabbit peritoneal macrophages. During the test the synovial cells are exposed over a 3 day period to a known amount of MCF sufficient to stimulate collagenase synthesis and secretion. Drugs are added at the same time as MCF. The culture media is assayed for collagenase using a collagen fibril assay. Hydrocortisone inhibits collagenase release at concentrations down to 1 ng/ml, and non-steroidal antiinflammatory drugs like naproxen fail to inhibit collagenase release at non-toxic concentrations.

The compound of Example 15 reproducibly inhibits collagenase release at non-toxic concentrations (e.g. 30 μg/ml).

No toxic effects were observed in any of the above described tests for the cited compounds at the indicated doses.

We claim:
1. A compound of formula (I) or a salt or solvate thereof:

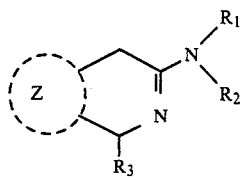

in which:
R₁ and R₂ are independently hydrogen or $C_{1-6}$ alkyl;
R₃ is phenyl, naphthyl, furyl, thienyl, pyrryl, pyridyl, benzofuranyl, benzothienyl or indolyl optionally substituted by one or more of fluoro, chloro, bromo, $CF_3$, nitro, methyl, ethyl, n- or iso-propyl, n-, sec- or tert-butyl, methoxy, ethoxy, n- or iso-propoxy, or, when R₃ is phenyl or naphthyl, optionally substituted by one or more of methylthio, ethylthio, n- or iso-propylthio, acetyl, propionyl, carboxyl, methoxycarbonyl, ethoxycarbonyl, cyano, $CONH_2$, $NR_9^1R_{10}^1$, in which $R_9^1$ and $R_{10}^1$ are independently selected from hydrogen, methyl, or methylsulphonyl or together are a group $X^1$ which is $C_4$ or $C_5$ polymethylene or —$(CH_2)_2$—O—$(CH_2)_2$—, $SO_2NR_{11}^1R_{12}^1$, in which $R_{11}^1$ and $R_{12}^1$ are independently selected from hydrogen or methyl, methylsulphonyl, ethylsulphonyl, methylsulphinyl or ethylsulphinyl;
Z is naphthyl, or, (when R₃ is other than phenyl or substituted phenyl), phenyl and Z is optionally C-substituted by one or two substituents $R_4^1$ and $R_5^1$ which are independently selected from methyl, ethyl, n- or iso-propyl, cyano, amino, aminocarbonyl or amino-carbamoyl optionally substituted by one or two methyl groups, fluoro, chloro, bromo, nitro, methoxy, hydroxy, acetoxy, n-butyryloxy or 2,2-dimethylpropionyloxy, or together on adjacent carbon atoms are methylenedioxy.

2. A compound according to claim 1 in which R₁ and R₂ independently are hydrogen, methyl, ethyl, n- or iso-propyl, n-, sec or tert-butyl.

3. A compound according to claim 1 in which Z is phenyl and R₃ is naphthyl or pyridyl optionally substituted by one or two of fluoro, chloro, bromo nitro, or methyl.

4. A compound according to claim 1 in which R₃ is pyridyl or is naphthyl optionally substituted by one or two of bromo, chloro or fluoro.

5. A compound according to claim 1 in which Z is naphthyl optionally substituted by one or two substituents $R_4^1$ and $R_5^1$ and R₃ is phenyl optionally substituted by one or two of fluoro, chloro, bromo nitro or methyl.

6. A compound according to claim 5 in which Z and R₃ are optionally substituted by one or two of bromo, chloro or fluoro.

7. A compound according to claim 1 selected from the group consisting of:
1-[1'-(4'-Chloronaphthyl)]-3-dimethylamino-1,4-dihydroisoquinoline;
1-[2'-(1'-Chloronaphthyl)]-3-dimethylamino-1,4-dihydroisoquinoline;
5-Chloro-1-(2'-chlorophenyl)-3-dimethylamino-1,4-dihydro-benz[g]isoquinoline;
5-Bromo-1-(2'-chlorophenyl)-3-dimethylamino-1,4-dihydro-benz[g]isoquinoline;
1-(2'-chlorophenyl)-3-dimethylamino-1,4-dihydro-benz[g]isoquinoline;
5-Chloro-1-(2'-fluorophenyl)-3-dimethylamino-1,4-dihydro-benz[g]isoquinoline;
5-Bromo-1-(2'-fluorophenyl)-3-dimethylamino-1,4-dihydro-benz[g]isoquinoline;
1-(2'-Fluorophenyl)-3-dimethylamino-1,4-dihydro-benz[g]isoquinoline;
4-(2'-Fluorophenyl)-2-dimethylamino-1,4-dihydro-benz[f]isoquinoline;
1-(2'-Fluorophenyl)-3-dimethylamino-1,4-dihydro-benz[h]isoquinoline;
6-Fluoro-4-(2'-chlorophenyl)-2-dimethylamino-1,4-dihydro-benz-[f]isoquinoline;
6-Bromo-4-(2'-fluorophenyl)-2-dimethylamino-1,4-dihydro-benz[f]isoquinoline;
1-(2'-Fluorophenyl)-3-dimethylamino-8-methoxy-1,4-dihydro-benz[h]isoquinoline;
1-(2'-Fluorophenyl)-3-dimethylamino-5-methoxy-1,4-dihydro-benz[g]isoquinoline;
1-(3'-pyridyl)-3-dimethylamino-1,4-dihydro-isoquinoline
1-(2'-Chloro-4'-pyridyl)-3-dimethylamino-1,4-dihydroisoquinoline;
5-Chloro-1-(3'-pyridyl)-3-dimethylamino-1,4-dihydroisoquinoline; or
6-Fluoro-1-(3'-pyridyl)-3-dimethylamino-1,4-dihydroisoquinoline.

8. A compound according to claim 1 in pharmaceutically acceptable form.

9. A pharmaceutical composition for the treatment of inflammatory conditions in mammals comprising a therapeutically effective amount of a compound as claimed in claim 1, or a pharmaceutically acceptable salt or solvate thereof, together with a pharmaceutically acceptable carrier.

10. A method of treating an inflammatory condition in mammals, which comprises administering an effective amount of a compound as claimed in claim 1, or a pharmaceutically acceptable salt or solvate thereof, to the mammal.

* * * * *